United States Patent [19]

Levine

[11] 4,252,784
[45] Feb. 24, 1981

[54] METHOD AND COMPOSITION FOR TESTING TO PREDICT AND/OR DIAGNOSE ALLERGY TO PENICILLINS

[76] Inventor: Bernard B. Levine, 210 Riverside Dr., New York, N.Y. 10025

[21] Appl. No.: 69,149

[22] Filed: Aug. 23, 1979

Related U.S. Application Data

[62] Division of Ser. No. 898,044, Apr. 20, 1978.

[51] Int. Cl.$^3$ .............................................. A61K 49/00
[52] U.S. Cl. ....................................... 424/9; 424/177; 424/271
[58] Field of Search ........................... 424/9, 177, 271

[56] References Cited

PUBLICATIONS

Levine et al., J. of Clin. Invt., vol. 47, Mar. 1968.
Levine et al., Int. Arch. of Allergy & Applied Immunol, vol. 35, 1969, pp. 445–455.
Levine et al., The J. of Allergy, vol. 43, Apr. 1969, pp. 231–244.
Levine, Sci. Writers Seminar, Allergic disease Res. Drug Allergy, Remarks, Jan. 26, 1971, 14 pp. (DHEW pub. 73-202).
Levine, J. of Med. & Pharm. Chem., vol. 5, 1962, pp. 1025–1034.

*Primary Examiner*—Anna P. Fagelson
*Attorney, Agent, or Firm*—Sughrue, Rothwell, Mion, Zinn and Macpeak

[57] ABSTRACT

The invention relates to the testing of humans or other animals, such as horses, cattle or dogs, for allergic reaction or hypersensitivity to penicillins. The tests can be used both to predict and to diagnose allergy. The invention comprises new penicilloyl-polylysine (PPL) preparations, and novel test methods employing such materials.

The new PPL preparations comprise homogeneous, high purity, maximally coupled, α-diastereoisomeric, penicilloyl conjugates of low molecular weight PPLs. The PPL materials of the invention have the molecular structure in accordance with the following generic formula:

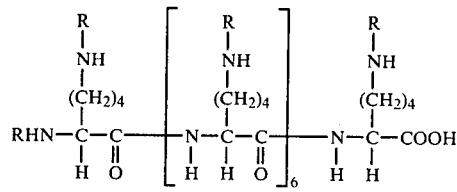

wherein:
R is selected from the group consisting of H and penicilloyl groups or similar groups derived from cephalosporins or other β-lactam antibiotics; and
n is an integer of from 4 to 10, at least about 66% and up to 100% of the R groups are other than hydrogen. Solutions containing this PPL material are useful in skin testing for penicillin allergy or hypersensitivity alone, but preferably are utilized in a two-part test with MDM solutions containing the novel MDM materials of the invention.

The tests are preferably carried out by applying solutions of the materials to the skin of the patient or other test animal and pricking or scratching the skin, or by injecting the materials intradermally, and then observing for wheal and flare reactions. The preferred test method comprises a two-solution test using a solution of the novel PPL preparations applied on or into one area of the patient's skin and a separate solution containing the new minor determinant material alone or as part of an MDM solution with other constituents applied on or into another area of the patient's skin.

4 Claims, No Drawings

METHOD AND COMPOSITION FOR TESTING TO PREDICT AND/OR DIAGNOSE ALLERGY TO PENICILLINS

This is a division of application Ser. No. 898,044, filed Apr. 20, 1978.

BACKGROUND OF THE INVENTION

1. Field of the Invention

The invention provides novel PPL materials and compositions and more sensitive tests for predicting and diagnosing allergy or hypersensitivity to penicillin in humans or other animals by skin testing with the improved PPL compositions of the invention.

2. Discussion of the Prior Art

Since the introduction of penicillins for therapeutic treatment of infections in humans and other animals, a variety of allergic reactions have been observed; the most serious of these reactions is anaphylactic shock, which is estimated to be the cause of several hundred deaths in the United States each year. The possibility of non-fatal anaphylaxis and urticarial reactions, which are much more common than fatal anaphylaxis, also is a matter of serious concern for the physician considering the treatment of a patient with penicillins.

Therefore, much research effort has been devoted to the development of reliable tests predictive of human allergic response or hypersensitivity to penicillin. As the result, certain skin tests have been described in the literature and are under study clinically. One such test generally involves scratching the skin in an area on which a test solution has been placed, or intradermally injecting the test solution, and observing for a positive reaction—i.e., a wheal-and-flare reaction around the scratch or injection sites formed within 15 minutes. More sensitive skin tests involve the inntradermal injection of solutions containing (1) PPL and (2) MDM (minon determinant mixtures) compositions.

The chemistry underlying the mechanism by which penicillin may trigger allergic reactions in humans and the details of the state of the art in "scratch" and "intradermal" skin tests is extensively set forth in the literature. The following are intended only as representative citations which provide useful technical background in the field of this invention:

"Immunological Mechanisms of Penicillin Allergy"
B. B. Levine; J. New England Medicine, 275:1115 (1966)

"The Nature of the Antigen-Antibody Complexes Initiating the Specific Wheal-and-Flare Reaction in Sensitized Man"
B. B. Levine, A. P. Redmond; J. Clinical Investigation, 47:556 (1968)

"Predictions of Penicillin Allergy by Immunological Tests"
B. B. Levine, D. M. Zolov; J. of Allergy, 43:4:231 (1969)

"Drug Allergy"
B. B. Levine; Reprint of Edited Remarks presented at seminar co-sponsored by Johns Hopkins U., Am. Acad. of Allergy and NIH (1971)

"Skin Rashes With Penicillin Therapy: Current Management"
B. B. Levine; New England Journal of Medicine (1971)

"A Guide to Skin Testing for Penicillin Allergy"
N. F. Adkinson, Jr., Resident and Staff Physician at Johns Hopkins U. (1977)

See also U.S. Pat. Nos. 3,867,365 and 3,979,508 issued to Stahmann and Wagle.

U.S. Pat. No. 3,867,365, noted above, describes one prior art PPL material used in penicillin allergy skin tests, and it is believed that such compounds may have been commercialized. The patented compositions over which my compositions are an improvement comprise BPO conjugates of a heterogeneous mixture of random polylysine polymers said to have from about 12 to 102 or more lysine units linked in the polymer chain.

In prior studies, such as those cited above, it has also been shown that some patients who are given penicillin therapeutically develop IgE antibodies to certain haptens which are formed from the reaction of the penicillin with tissue proteins. These include the benzylpenicilloyl (BPO) hapten, whose structure is well known, and certain "minor determinant" haptens whose structures are not yet known.

IgE antibodies are known to mediate anaphylactic and other immediate allergic reactions to penicillin in man. These reactions are frequently severe, causing diffuse rash, difficulty in breathing, abdominal cramps and fainting, hypotension and arrythmia. They are capable of causing death due to cardiovascular collapse, ventricular arrythmia and/or respiratory obstruction.

Skin tests with various materials derived from penicillin have been shown to be positive in the presence of these IgE antibodies, and thus serve as a predictive test for severe penicillin allergy. The skin test compositions currently in use include benzylpenicilloyl-polylysine (BPL), which detects IgE antibodies specific for the BPO haptenic group, and the MDM, which detects IgE antibodies specific for the minor determinants.

With respect to my new PPL materials, I have observed a number of significant improvements over the prior art. First, my PPL materials are homogeneous, high purity materials which offer higher reproducibility from lot to lot than is provided by heterogeneous polylysine conjugates of the prior art. The new PPL materials of this invention also are substantially free from low molecular weight impurities (polylysine$_2$ and/or polylysine$_3$) and, therefore, minimize the chance of diffusion of compound from the test site into the bloodstream with the attendant possibility of constitutional reactions. Additionally, my relatively low molecular weight, $B_{4-13}$—$L_{6-12}$, materials would have a lower degree of immunogenicity than the higher molecular weight PPL conjugates of the prior art, and, thus, are less likely to induce allergy in a test subject. Further my PPL materials are of a molecular weight which allows sufficient diffusion in the skin from an intradermal or prick test site to give an intense wheal-and-flare reaction. By contrast, high molecular weight conjugates may diffuse less well in about one-fourth to one-third of patients and, thus, may not give a recognizably positive skin test in some allergic patients (Levine and Fellner, Journal of Allergy, 36:342-52 (1965)).

In view of the possibly catastrophic consequences of observing a negative response in a patient who is actually allergic to penicillin, it is critical that the most sensitive and highly reliable allergy tests be made clinically available.

Further, the use of the most sensitive test is of importance when doing prick or scratch tests. These are much more convenient but less sensitive than intradermal tests. Thus, more sensitive test materials permit the use of a prick test.

Accordingly, the principal objective of my invention is to provide a more sensitive and reproducible skin test for penicillin allergy using improved PPL preparations. Another purpose is to provide novel PPL and MDM compounds and compositions for use in skin testing for prediction or diagnosis of penicillin allergic reaction or hypersensitivity.

SUMMARY OF THE INVENTION

My invention comprises:

(1) New PPL preparations. The penicilloyl groups are the $\alpha$-diastereoisomers. The polylysine carriers are linear homogeneous polymers having a degree of polymerization of from 6 to 12. The polylysine polymers may be prepared from L-, D-, or D,AL-lysines. These polymers are maximally coupled with penicilloyl groups. For example, in one material, the poly-L-lysine$_8$ carrier was over 97% pure, the balance being polylysine$_{6-7}$. This material was maximally coupled with 8 penicilloyl moieties. In other preparations of this PPL, from 6 to 9 penicilloyl moieties may be coupled to the polylysine$_8$ polymer chain.

(2) Methods for skin testing for penicillin allergy or hypersensitivity using solutions containing the novel materials of (1) independently or in a two-solution, combined test. The skin tests may be prick, scratch or intradermal. Some of the compositions may also be useful for in vitro testing for penicillin allergy.

DETAILED DESCRIPTION OF THE INVENTION

My invention will be more fully appreciated in view of the following detailed description of certain preferred embodiments.

Benzylpenicilloyl$_8$-Poly-L-Lysine$_8$ ($B_8L_8$)

1. Preparation

The PPL materials of my invention comprise a homogeneous polylysine carrier of from 6 to 12 degrees of polymerization in which at least about 66% of the coupling sites are occupied by conjugated penicilloyl groups derived from penicillins, cephalosporins or other $\beta$-lactam antibiotic moieties.

The novel $B_8L_8$ which is within the scope of my invention was prepared in the following manner:

Octa-L-lysine was prepared by the procedure of L. E. Barstow, et al. (Proc. Natl. Acad. Sci. U.S.A. 74:4248, 1977), with the following modifications. The starting material was $\alpha$-t-BOC$\epsilon$CBZ-L-lysine Merryfield resin ester. There were seven consecutive couplings with $\alpha$-t-BOC$\epsilon$CBZ-L-lysine with intermediate deprotection of the $\alpha$-NH$_2$ group using trifluoracetic acid (TFA). The resulting octa-L-lysine was deprotected and cleaved from the resin by mixing the resin at 25° C. for 25 minutes with TFA saturated with HBr gas (1 g resin per 10 ml TFA). HBr was removed by N$_2$ purge, and TFA was removed by evporation under vacuum. The product was dissolved in H$_2$O and lyophilized. The residue was then dissolved in 50% acetic acid and purified by chromatography through Sephadex G-15. The solution containing the major peak was diluted with H$_2$O to 10% acetic acid and lyophilized to yield a slightly yellow amorphous powder. The material was analyzed by paper chromatography using a modified Waley-Watson system (B. B. Levine and A. P. Redmond, J. Clinical Investigation 47:556, 1968). It showed one major spot corresponding to octa-L-lysine with traces at lysine$_6$ and lysine$_7$ (corresponding in color intensity to about 1% each).

100 mg of poly-L-lysine$_8$.HBr (assuming 90% peptide, 10% water) was dissolved in 25 ml deionized water and the pH was brought to $10\pm0.3$ with 0.5 M NaOH. A solution of 755 mg of potassium PG in 10 ml of water was added and the pH was brought to $11.5\pm0.05$ with 0.5 M NaOH. The reaction proceeded at room temperature (T=22° C.) with the reaction solution stirred by a magnetic stirrer and the pH maintained at $11.5\pm0.05$ by additions of the 0.5 M NaOH. After two hours, when the reaction had gone to completion as evidenced by stability of the pH at 11.5, the solution was cooled to 5°-10° C. in an ice bath. The pH was brought down to pH 3.6 by additions of 1 N HCl to the stirred solution. The white precipitate that formed was centrifuged down in a cold centrifuge. The precipitate was washed twice with small quantities of ice-cold deionized water. The precipitate was suspended in 20 ml of deionized water and dissolved by bringing the pH to 9.5-10.5 with 0.5 M NaOH. The solution was clarified by cold centrifugation. The solution was cooled to 5°-10° C. and brought to pH 3.6 with 1 N HCl. The white precipitate was centrifuged down and washed three times with small quantities of ice-cold deionized water. The moist precipitate was dried under very high vacuum in a lyophylizer. The yield was equal to 104 mg white powder about 55% of the theoretical.

In addition to the polylysine$_8$ derivative of PG described above, polylysine$_8$ derivatives can be prepared from all semi-synthetic penicillins. Thus, ampicillin, carbenicillin, naphthacillin, oxacillin, cloxacillin, staphcillin, phenoxyethylpenicillin, phenoxymethylpenicillin, piparicillin, mezlocillin, etc. can be used to prepare corresponding PPL$_8$ derivatives. It is also expected to be possible to prepare useful polylysine$_8$ derivatives from cephalosporins and other $\beta$-lactam antibiotics. Methods other than precipitation at pH 3.7 can be used to isolate this or other final products, for example, preparative chromatographic methods or membrane separations may be used.

2. Preparation Of Test Solution

A solution for use in skin testing for penicillin allergy or hypersensitivity using the above-described $B_8L_8$ was prepared as follows:

1.00 mg/ml was dissolved in 0.05 M Na$_2$HPO$_4$. This was assayed by penamaldate assay which indicated the BPO concentration to be equal to $1.90\times10^{-3}$ M. The total nitrogen content was assayed by the micro-Kjeldahl method and was determined to be 106 $\mu$g/ml. The nitrogen contribution from BPO was determined to be equal to $1.90\times28$ $\mu$g/ml or 53 $\mu$g/ml. The nitrogen contribution from polylysine$_8$ was determined to be equal to 106-53 or 53 $\mu$g/ml. The polylysine$_8$ equals $53\times4.65$ or 246 $\mu$g/ml which, when divided by 1042, equals $2.37\times10^{-4}$ M. The number of BPO groups per mol of polylysine$_8$ was calculated to be 8.02. Thus, the conjugate was determined to be $B_8L_8$, and the concentration of $B_8L_8$ in the stock solution of 1.00 mg/ml of $B_8L_8$ was determined to be $2.37\times10^{-4}$ M.

3. Skin Tests Utilizing The $B_8L_8$ Solution

Skin testing using the novel $B_8L_8$ solution was conducted as follows:

The $B_8L_8$ stock solution was diluted to $1\times10^{-6}$ molar in tris-buffered saline with a pH of 8.2, also containing ethylenediaminetetraceticacid ($2\times10^{-4}$ molar) for stability. The composition was then used in skin testing. The tests were conducted by both the prick test and intradermal test methods, and the results were as follows:

Patient No. 1—prick test—$B_8L_8=2+$. The appearance of erythema and the size of the wheal (4–5 mm in diameter) indicated a positive reaction to the $B_8L_8$.

Patient No. 2—intradermal test—the $B_8L_8$ gave a 10 mm wheal and rated from $2+$ to $3+$ in intensity.

Other concentrations of the new PPL material can also be used for testing.

Additional non-allergic patients were tested in a similar fashion and showed negative reactions, indicating that the solutions were not primary irritants.

What is claimed is:

1. A composition of matter for skin testing for allergy or hypersensitivity to penicillins, including benzyl penicillin and semi-synthetic penicillins, by the detection of skin sensitizing antibodies formed in the body of a patient upon the administration of penicillins in response to the formation of the benzylpenicilloyl hapten comprising prick, scratch, or intradermal testing of the skin of a patient with solutions comprising (a) substantially homogeneous penicilloyl-polylysine conjugates represented by the formula:

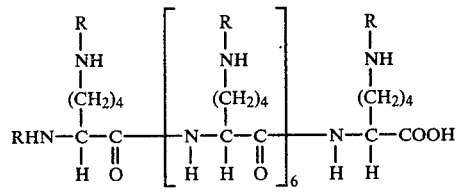

wherein:
    R is selected from the group consisting of H and penicilloyl groups derived from penicillins, cephalosporins or other $\beta$-lactam antibiotics, and at least about 66% and up to 100% of the R groups are other than hydrogen; and
    the linear polylysines are selected from the group consisting of poly-L-lysines, poly-D-lysines and poly-D,L-lysines, and
    (b) a suitable solvent for said conjugate (a), said solvent being compatible with the use of said composition in skin testing for penicillin allergy or hypersensitivity to penicillins, including benzyl penicillin and semi-synthetic penicillins,
    the concentration of said conjugate (a) in said solvent (b) being sufficient to elicit a wheal and flare response in patients allergic or potentially allergic to said penicillins when said composition is administered to said patient in said skin testing but said concentration being optimal to avoid a constitutional reaction.

2. The composition of claim 1 wherein said solvent is an aqueous buffered saline solution.

3. A method for skin testing for allergy or hypersensitivity to penicillins, including benzyl penicillin and semi-synthetic penicillins, by the detection of skin sensitizing antibodies formed in the body of a patient upon the administration of penicillins in response to the formation of the benzylpenicilloyl hapten comprising prick, scratch, or intradermal testing of the skin of a patient with solutions comprising (a) substantially homogeneous penicilloyl-polylysine conjugates represented by the formula:

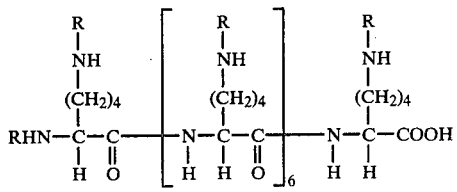

wherein:
    R is selected from the group consisting of H and penicilloyl groups derived from penicillins, cephalosporins or other $\beta$-lactam antibiotics, and at least about 66% and up to 100% of the R groups are other than hydrogen; and
    the linear polylysines are selected from the group consisting of poly-L-lysines, poly-D-lysines and poly-D,L-lysines, and
    (b) a suitable solvent for said conjugate (a), said solvent being compatible with the use of said composition in skin testing for penicillin allergy or hypersensitivity to penicillins, including benzyl penicillin and semi-synthetic penicillins,
    the concentration of said conjugate (a) in said solvent (b) being sufficient to elicit a wheal and flare response in patients allergic or potentially allergic to said penicillins when said composition is administered to said patient in said skin testing but said concentration being optimal to avoid a constitutional reaction.

4. The method of claim 3 wherein said solvent is an aqueous buffered saline solution.

* * * * *